United States Patent
Steinle et al.

(10) Patent No.: US 10,925,492 B2
(45) Date of Patent: Feb. 23, 2021

(54) ATLAS-BASED PRODUCTION OF A MEDICAL SUPPORT DEVICE

(71) Applicant: Brainlab AG, Munich (DE)

(72) Inventors: Wolfgang Steinle, Munich (DE); Christoffer Hamilton, Aschheim (DE); Nils Frielinghaus, Heimstetten (DE)

(73) Assignee: BRAINLAB AG, Munich (DE)

( * ) Notice: Subject to any disclaimer, the term of this patent is extended or adjusted under 35 U.S.C. 154(b) by 1182 days.

(21) Appl. No.: 15/120,507

(22) PCT Filed: Feb. 21, 2014

(86) PCT No.: PCT/EP2014/053411
§ 371 (c)(1),
(2) Date: Aug. 19, 2016

(87) PCT Pub. No.: WO2015/124199
PCT Pub. Date: Aug. 27, 2015

(65) Prior Publication Data
US 2017/0065176 A1   Mar. 9, 2017

(51) Int. Cl.
*A61B 6/04* (2006.01)
*A61G 13/12* (2006.01)
(Continued)

(52) U.S. Cl.
CPC .......... *A61B 5/0037* (2013.01); *A61B 5/0555* (2013.01); *A61B 5/4887* (2013.01);
(Continued)

(58) Field of Classification Search
CPC .. A61G 31/121; A61G 13/121; B29C 64/386; A61B 90/14; A61B 34/20; A61B 5/4887;
(Continued)

(56) References Cited

U.S. PATENT DOCUMENTS 5,566,681 A * 10/1996 Manwaring ............ A61G 13/12
  128/845
5,966,763 A * 10/1999 Thomas .................. A61G 13/12
  5/715
(Continued)

FOREIGN PATENT DOCUMENTS

| EP | 2110079 | 10/2009 |
| EP | 3107458 A1 | 12/2016 |
| WO | WO2015124199 A1 | 8/2015 |

OTHER PUBLICATIONS

Hohne, K.H., et al. "A 'Virtual Body' Model for Surgical Education and Rehearsal" Computer, vol. 29, issue 1 (1996) (Year: 1996).*
(Continued)

*Primary Examiner* — Jay Hann
(74) *Attorney, Agent, or Firm* — Middleton Reutlinger (57) ABSTRACT

A system and method of producing a medical support device is disclosed. The disclosure determining a three-dimensional shape of the medical support device for supporting an anatomical body part of a patient, the method executed by a computer and including acquiring body part geometry data describing a geometry of the anatomical body part; acquiring medical procedure data describing a medical procedure to be carried out on the patient; acquiring atlas data describing a general three-dimensional shape of the anatomical body part; determining, based on the body part geometry data and the medical procedure data and the atlas data, support device geometry data describing the geometry of the support device. The method and system further includes generative forming of the device by issuing at least one control command to the generative forming device for forming the medical support device based on the support device geometry data.

12 Claims, 2 Drawing Sheets

(51) Int. Cl.
| | |
|---|---|
| *A61B 90/14* | (2016.01) |
| *B29C 64/386* | (2017.01) |
| *G16H 50/50* | (2018.01) |
| *A61B 34/20* | (2016.01) |
| *A61B 5/00* | (2006.01) |
| *A61B 6/03* | (2006.01) |
| *A61B 8/00* | (2006.01) |
| *A61B 5/055* | (2006.01) |
| *B33Y 80/00* | (2015.01) |
| *A61N 5/10* | (2006.01) |
| *A61B 17/00* | (2006.01) |

(52) U.S. Cl.
CPC ............ *A61B 6/032* (2013.01); *A61B 6/04* (2013.01); *A61B 8/40* (2013.01); *A61B 34/20* (2016.02); *A61B 90/14* (2016.02); *A61G 13/121* (2013.01); *B29C 64/386* (2017.08); *A61B 2017/00526* (2013.01); *A61B 2034/2055* (2016.02); *A61B 2034/2065* (2016.02); *A61N 2005/1097* (2013.01); *B33Y 80/00* (2014.12); *G16H 50/50* (2018.01)

(58) Field of Classification Search
CPC ......... A61B 5/0037; A61B 6/032; A61B 6/04; A61B 8/40; A61B 5/0555; A61B 2034/2065; A61B 2034/2055; A61B 2017/00526; B33Y 80/00; A61N 2005/1097; G16H 50/50
See application file for complete search history.

(56) References Cited

U.S. PATENT DOCUMENTS

| | | | |
|---|---|---|---|
| 6,459,927 | B1 | 10/2002 | Franklin et al. |
| 7,234,180 | B2 * | 6/2007 | Horton ............... A61G 13/12 5/613 |
| 7,340,316 | B2 * | 3/2008 | Spaeth ............... G16H 50/50 700/98 |
| 9,189,886 | B2 * | 11/2015 | Black .................. G06T 7/75 |
| 9,469,075 | B2 * | 10/2016 | Zachariasen ........ G06F 30/17 |
| 2012/0265496 | A1 | 10/2012 | Mahfouz |
| 2013/0211531 | A1 * | 8/2013 | Steines ............. A61F 2/4684 623/20.35 |
| 2019/0378276 | A1 * | 12/2019 | Flossmann ........... G06T 7/344 |

OTHER PUBLICATIONS

European Patent Office; International Search Report for PCT/EP2014/053411 dated Nov. 4, 2014.
European Patent Office: Decision to Grant issued for application 14706813.4 dated Aug. 17, 2018. (2 Pages).
European Patent Office: Intention to Grant issued for application 14706813.4 dated Jun. 1, 2018. (1 Pages).
European Patent Office: Text Intended to Grant issued for application 14706813.4 dated Jun. 1, 2018. (27 Pages).

* cited by examiner

Fig. 1

ATLAS-BASED PRODUCTION OF A MEDICAL SUPPORT DEVICE

The present invention relates to a method, in particular a data processing method, of determining a three-dimensional shape of a medical support device such as a head rest for supporting an anatomical body part of a patient such as his head. The invention also relates to a corresponding program and a computer running that program as well as to the medial support device itself. Furthermore, the invention relates to a method of producing the medical support device which comprises in particular execution of the aforementioned data processing method.

When conducting a medical procedure such as neurosurgery or radiotherapy, it is desirable to have the target region such as a part of the brain at a well-defined position which is preferably known to a navigation system and/or a patient positioning system. The navigation system and/or patient positioning system comprises a computer conducting the data processing for the radiotherapy such that the treatment beam can be brought into a predetermined spatial relationship relative to the target region. To this end, patient-specific support devices such as head fixtures are commonly used which are formed for example by a rapid fabrication process.

A rapid fabrication process such as a three-dimensional printing process is a generative manufacturing process for manufacturing a structure in which the structure is generated lay-by-layer from e.g. a powder which is irradiated with light of well-defined energy such as laser light to mold the powder particles together, thereby generating the structure according to e.g. geometric input data defining an in particular predetermined shape.

For example, U.S. Pat. No. 6,459,927 B2 discloses a method for fabricating a customized positioning fixture for a patient's head in which a rapid prototyping and tooling (RPT) technique is used to fabricate the fixture. Information about the geometry of the patient's head is acquired from a scanned image of the patient for patient-specific customization of the fixture.

Likewise, U.S. Pat. No. 6,459,927 B1 shows production of a patient-specific mask such as a biopsy probe holder by application of an RPT technique. A three-dimensional dataset is generated from a series of two-dimensional CT or MRI scanner images and used as an input for the RPT technique.

These methods, however, do not take into account specifics of a patient's anatomy and may therefore lead to production of a patient support device such as a fixture or a mask which does not allow for a comfortable use. For example, the current standard of care in neurosurgery is a metal head clamp which requires the doctor to hold the head in the right pose for surgery while another person fixates the clamp. This process is cumbersome and requires very qualified personnel during this early stage of the procedure. Additionally, there is the risk that the head drops during this process or later on during surgery. The present invention allows for positioning the patient without specific clinical knowledge and there is no risk for the head dropping.

The present invention can be used with Brainlab's navigation system and/or a patient positioning system, such as electro-magnetic surgical navigation system, navigation system using optical tracking, intraoperative ultrasound, intraoperative MRI and/or mobile intraoperative computed tomography, particularly with Brainlab's platforms like Curve™ Image-Guided Surgery, Kick® Purely Navigation, Kick® EM, Airo® Mobile Intraoperative CT and Buzz™ Digital O.R.

A problem to be solved by the present invention therefore is to provide an improved method of determining the shape of a medical support device which in particular leads to production of a support device which stably supports the patient and is easy to use.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

EXEMPLARY SHORT DESCRIPTION OF THE PRESENT INVENTION

In the following, a short description of specific features of the present invention is given which shall not be understood to limit the invention only to the features or a combination of the features described in this section.

The invention relates in particular to a data processing method which determines (i.e. has as an output) geometric input data for a generative manufacturing process such as a rapid fabrication process (e.g. a rapid prototyping process) for producing a structure which may be a support device (for example a fixture, in particular a head rest) for supporting an anatomical body part of the patient by e.g. a rapid prototyping process. The geometric input data for the rapid prototyping process is determined based on in particular atlas information describing a statistical model of the anatomical body part. The geometric input data may according to one embodiment also determine such that not only a support for the anatomical body part is determined but such that the support device comprises additional equipment (in the framework of this disclosure called "medical accessory"), for example a hand rest for a surgeon or a drain part.

The invention also relates to a program comprising code means for executing the data processing method. It also relates to a computer running that program. A method for producing the support device which comprises execution of the aforementioned data processing method and/or computer program is also part of the invention.

Furthermore, the invention also relates to the support device itself which has been in particular produced by the aforementioned production method.

GENERAL DESCRIPTION OF THE PRESENT INVENTION

In this section, a description of the general, in particular preferred, features of the invention is given.

In order to solve the aforementioned problem, in particular a medical data processing method of determining a three-dimensional shape of a medical support device is provided. The medical support device (in the framework of this disclosure also called "support device") is suitable to support an anatomical body part of a patient. The anatomical body part may be any anatomical body part. According to a preferred embodiment, the support device is a fixture for positioning the patient's head, in particular a head rest and the anatomical body part is the patient's skull or head, respectively.

The method is preferably constituted to be executed by a computer. In particular, it is constituted to be at least partly executed by a computer, i.e. all the steps are merely some of the steps (i.e. less than the total number of steps) of the method in accordance with the invention can be, in particular, are executed by a computer. The inventive method comprises the following preferred steps.

Preferably, body part geometry data is acquired which describes (in particular defines, more particularly represents and/or is) (in particular defines, more particularly represents and/or is) a geometry of the patient's anatomy, in particular of the anatomical body part. In particular, the geometry is defined by at least one of the size (in particular dimensions and/or volume) and shape (e.g. values defining angles and positions of specific anatomical features, e.g. of hard tissue such as bones and bones, and of soft tissue such as skin or muscles) relative to each other. Such information constitutes a "geometric definition" of the anatomical body part and is contained in the body part geometry data in particular as numeric values for example in a table format. According to another (alternative or additional) embodiment which is described further below, the body part geometry data may have been acquired from or may comprise medical image data describing an image of the anatomical body part. Additionally, the body part geometry data preferably comprises information defining for example the type of body part which the anatomical body part represents. For example, the body part geometry data may specify that the anatomical body part is the back of the patient's head, his face, chin and (upper and/or lower) neck. In the framework of this disclosure, such information is also called "typologic definition" of the anatomical body part.

Preferably, medical procedure data is acquired which describes (in particular defines, more particularly represents) an envisaged medical procedure to be carried out on the patient. For example, the medical procedure data indicates that the envisaged medical procedure is tumour therapy by infusion of a substance through a catheter into the brain or by radiotherapy of the brain. Alternatively or additionally, the medical procedure data may indicate that the envisaged medical procedure is brain surgery which in particular requires an access path, for example opening in the patient's skull. Preferably, the medical procedure data describes the position of an anatomical target region or an access path associated with the envisaged medical procedure such as the aforementioned opening in the skull through which a medical instrument such as a catheter or an electrocautery can be inserted into the patient's body, in particular into the aforementioned anatomical body part. The access path may also describe a trajectory along which a medical instrument is to be placed in a predetermined spatial relationship relative to the anatomical body part. For example, the access path describes a trajectory along which a drill is to be positioned relative to the patient's skull. The anatomical target region constitutes the region at which the envisaged medical procedure shall have a desired (in particular therapeutic) effect. The anatomical target region therefore comprises in particular pathologic tissue such as a tumour.

Preferably, atlas data is acquired which describes (in particular defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. In particular, the atlas constitutes a statistical model of a patient's body (in particular, a part of the body) which has been generated from anatomic information gathered from a plurality of human bodies, in particular from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes in particular the anatomy of the human bodies and is extracted for example from medical image information about the human bodies. The atlas data preferably comprises positional information describing the position of specific anatomic features such as different tissue type (e.g. hard tissue such as bones or cartilage and soft tissue such as skin, muscles or tissue of internal organs). The tissue types are preferably grouped into tissue classes which are defined e.g. by their absorbance for imaging radiation applied by a medical imaging modality used to gather the image information which serves as basis for generating the atlas. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the anatomical body part is the back of the patient's head (i.e. the respective part of the skull and the overlying tissue such as fat and skin as well as blood vessels). The atlas data then preferably describes the general three-dimensional shape of the (exterior) surface of the back of the patient's head. The atlas data is preferably acquired based on the body part geometry data, in particular based on at least one of the geometric and the typological definition of the anatomical body part by the body part geometry data. For example, the atlas of the anatomical body part is selected to fit the definition of the anatomical body part with regard to at least one of the above-mentioned features which are part of at least one of the geometric and typologic definitions. Preferably, the atlas is also selected such that it represents the anatomical body part according to the above-described specification by the body part geometry data. In particular, it is not necessary that the atlas data describes a general three-dimensional shape of a whole body of a patient. Rather, it is enough that the atlas data describes a statistic model of only the anatomical body part. For example, if the body part geometry data indicates that the anatomical body part is the patient's upper neck and the back of his head, it will suffice that the atlas data describes a statistical model of only those two body parts. According to a preferred embodiment, support positions of the anatomical body part are determined based on (in particular from) the atlas data. These support positions indicate positions on in particular the exterior surface of the statistical model of the anatomical body part on which the patient's head may be supported by the support device. The support positions preferably are of finite extent and disjunct from one another.

The support device is suitable in particular for supporting the anatomical body part during therapy such as tumour therapy by infusion, surgery or. Such therapies may require quite some time for conducting so that a need arises to avoid in particular tissue damage due to long periods of lying. To this end, the atlas data preferably comprises tissue information describing properties (in particular mechanical properties) of the tissue of the anatomical body part, for example of the fat and skin tissue of the back of the patient's head. The support positions are therefore preferably determined based on the tissue information, for example such that the support positions are selected to have the patient's head supported at positions which are particularly suitable for this purpose with regard to for example thickness of the fat and skin tissue and/or specific geometric features which might eventually cause pain or damage to the patient's skin if the patient's head rests too long on them. Furthermore, the support positions are preferably determined such that damage to or irritation of sensitive anatomic structures such as ears or eyes is avoided when the patient is supported by the support device.

Preferably, support device geometry data is determined based on the body part geometry data and the medical procedure data and the atlas data. The support device geometry data describes (in particular defines, more particularly represents and/or is) in particular the geometry, more particularly the three-dimensional geometry, of the support device. In particular, the geometry of the support device is therefore determined. The term of geometry encompasses the shape, size and preferably also material density of the support device. The geometry of the support device is preferably determined such that the support device provides an access path described by the medical procedure data, for example by providing openings in the support device through which a medical instrument such as a catheter, electrocauter or other probe may be inserted. Preferably, the geometry of the support device is determined such that also the position of the anatomical target region described by the medical procedure data is considered. For example, the geometry of the support device may be determined such that the support device has an opening at a position through which a treatment beam is to be directed for irradiating the anatomical target region with treatment radiation. Further preferably, the geometry of the support device is determined such that the surface of the support device on which the anatomical body part is to be placed is configured to support the anatomical body part. In particular, the geometry of the support device is determined such that there exists at least partly a form fit between the anatomical body part and the support device and that the distribution of the weight of the anatomical body part on the support device is as desired so as to in particular avoid injury to the anatomical body part. In particular, the geometry of the support device is determined such that the support device supports the anatomical body part at this port positions determined based on the atlas data.

According to a further specific embodiment of the invention, the body part geometry data has (preferably outside of the disclosed method, i.e. before the disclosed method is executed) been acquired from medical image data describing (in particular defining, more particularly representing and/or being) an image of the anatomical body part of the specific patient. Alternatively or additionally, the body part geometry data preferably comprises such medical image data. The medical image data may be used as a preferred additional basis for determining the support device geometry data. For example, medical image data may be acquired which describes (in particular defines, more particularly represents and/or is) the anatomical body part. The medical image data has been generated in particular by applying a medical imaging modality such as computed tomography, conventional x-ray or magnetic resonance imaging to the anatomical body part. Using a medical imaging modality which generates three-dimensional medical image information such computed tomography imaging or magnetic resonance imaging is preferred. The medical image data thus acquired is then preferably compared to the atlas data in order to determine the position of an anatomical structure in the description of the anatomical body part by the atlas data. In particular, the medical image data is used as a basis for acquiring, in particular selecting, suitable atlas data from a database. For example, the medical image data is compared to a plurality of atlas data sets each describing a specific atlas (e.g. for at least one of a specific type of gender, age, ethnicity, body size and pathologic state of the patient). The comparison between the medical image data and the atlas data is performed preferably by conducting a fusion (e.g. image fusion) procedure between the medical image data and the sets of atlas data. The set of atlas data for which the highest similarity between the definition of the geometry of the anatomical body part by the medical image data and the atlas data is determined is then selected as the atlas data to serve as a basis for determining the support device geometry data. The atlas data may also be contained in a universal atlas which is valid for any type of patient. In that case, it is not necessary to specifically search for and select a suitable atlas. In that case, it will suffice to determine the position of the above-described anatomical structure by mere comparison (e.g. fusion) between the atlas data of the universal atlas and the medical image data.

For example, the anatomical structure represents an anatomical target region, in particular a tumour. Alternatively or additionally, the anatomical structure may represent a sensitive organ such as an ear, the nose, the mouth or an eye of the patient's body. Even further alternatively or additionally, the anatomical region may represent a landmark, in particular, an anatomical landmark. The anatomical structure therefore does not need to be identical to the anatomical body part. Rather, the anatomical body part serves as a basis for determining the position of the anatomical structure in a body atlas (in particular, full-body atlas) described by the atlas data. The atlas has been in particular determined to comprise a suitable representation of the anatomical body part is determined based on the body part geometry data. [NF: typo geometry] As explained above, the medical image data may serve as a basis for determining the suitable atlas (i.e. for acquiring the atlas data), for example by comparing the description of the anatomical body part in the medical image data with the description of the respective anatomical body part in a plurality of atlases. The position of the anatomical structure is then determined from the thus-selected suitable atlas which contains a suitable (i.e. matching and/or fitting, in particular to a predetermined degree similar) representation of the anatomical body part. For example, the anatomical body part is the patient's skull and an atlas which contains a comparable representation of a skull is determined based on the specification of the anatomical body part contained in the patient's specification data and—according to an advantageous embodiment—based additionally on the medical image data of the anatomical body part. Once this suitable atlas has been determined, the position of the desired anatomical structures such as the nose in that atlas may be determined.

The support device geometry data is then preferably determined based on the position of the anatomical structure in the body atlas which is described by the atlas data. In particular, determining the support device geometry data comprises the above-mentioned comparison of the atlas data with the medical image data. In the above example, the position of the nose in the body atlas may be determined based on the body atlas which contains the suitable representation of the skull. On this basis, the geometry of a for example mask-shaped support device for the patient's head which also covers part of the face may be determined such that the support device has an opening at the position of the patient's nose. This provides the advantage of allowing the patient to breathe freely while the envisaged medical procedure is being conducted. As another example, the anatomical structure may be the patient's eyes, and their position in the body atlas is determined in a manner which is analogous to the aforementioned way of determining the position of the nose. In doing so, the geometry of the support device may be determined such that the support device has openings at the positions of the patient's eyes in order to allow the patient to look through the mask-shaped support device while conducting the envisaged medical procedure. This will have a beneficial psychological effect on the patient's wellbeing. The disclosed method therefore provides the advantage of having optimal knowledge about the position of such anatomical structures such as sensitive organs relative to the patient support device.

The disclosed method preferably also acquires accessory data comprising information about the geometry of medical accessory which is in particular to be disposed on the support device. The support device geometry data is then preferably determined based on also the accessory data, in particular the support device geometry data is determined such that it describes also the geometry of the medical accessory. For example, the support device geometry data may then describe that the geometry of the support device includes the geometry of the medical accessory. In particular, the geometry of the support device may then be determined such that all parts of the support device are integrally formed, in particular such that the support device is integrally formed with the medical accessory. The support device geometry data then preferably contains information which describes that the medical accessory is disposed integrally on the support device.

The medical accessory is preferably at least one of the following:
  a drain part for draining a liquid;
  an instrument support for supporting a medical instrument such as a catheter;
  a hand rest for a user's hand, the user not being identical to the patient (for example for the medical practitioner's hand who is conducting the envisaged medical procedure on the patient);
  a fixation unit for fixing the support device to a patient bed such as a clamp or a bracket;
  a mounting interface for mounting the support device to the patient, for example a handle or a click fastener;
  a marking (in particular at least one of a divot, a through-hole and a graphical feature) having a predetermined spatial relationship to the anatomical body part and/or being a marker device for detection by a navigation system;
  an opening for placing in the vicinity of a sensitive body part of the patient.

The marking can be an engraving or a colour mark which has a predetermined position relative to the anatomical body part, wherein the spatial relationship between the marking and the position of the anatomical body part is known to the user. For example, the marking may designate the desired position of at least part of the anatomical body part relative to the support device in order to help the user to align the support device correctly relative to the anatomical body part when supporting it on the support device. The marking can also be a marker device which preferably comprises, in particular is embodied by, a Moiré pattern and thus is video-detectable.

Preferably, initial geometry data is acquired which describes (in particular defines, more particularly represents and/or is) an initial geometry of a material for producing the support device, in particular of a material from which the support device shall be produced. The support device geometry data is then preferably determined based on also the initial geometry data. For example, the initial geometry may be represented by a volume of the material such as a solid block, from which parts are removed in accordance with the requirements described by in particular the medical procedure data and the atlas data so as to generate the geometry of the support device. This is an example of the preferred feature of the inventive method according to which the support device geometry data is determined by removing (in particular subtracting) a dataset describing the shape volume of the material from the initial geometry data, in particular this arithmetic and/or data processing operation relates to removing (in particular subtracting) the shaped volume of the material from the initial geometry. The removed (in particular subtracted) shaped volume corresponds to the volume of the material which is not required to form the geometry of the support device, in particular it represents excess material. The material preferably is a material which is suitable for processing by a generative manufacturing process (also called generative forming process or rapid prototyping technique), such as stereolithography, wide-area inkjet, selective laser sintering, fused deposition modelling, single-jet inkjet, three-dimensional printing and laminated object manufacturing. Any suitable rapid prototyping method (also called rapid fabrication method rapid fabrication process or rapid prototyping process) and material suitable for the respective method can be used to produce the support device. To this end, the invention also provides a method of producing the support device which comprises executing the above-described data processing method or the corresponding program on an electronic data processing device (in particular a computer), and producing the support device based on the support device geometry data. In order to support this, the support device geometry data is preferably determined in a digital form that makes the support device geometry data suitable as input data for a rapid prototyping process (also called rapid prototyping method), in particular a three-dimensional printing process. This digital format preferably is the surface tessellation language (STL) format which serves in particular as a quasi-standard interface for many computer-aided design systems. The support device is produced in particular by executing one of the aforementioned rapid prototyping methods and using the support device geometry data as an input for the rapid prototyping method.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, in particular electrical, in particular technically generated) signal wave, in particular a digital signal wave, carrying information which represents the program, in particular the aforementioned program, which in particular comprises code means which are adapted to perform any or all of the method steps described herein.

The invention also relates to the above-mentioned medical support device for supporting an anatomical body part of a patient, wherein the medical support device is a structure which has been generated by preferably one of the aforementioned rapid prototyping processes. The support device preferably includes a support surface having a geometry which is adapted to the geometry of the anatomical body part. In particular, the support surface is constituted to lie opposite (and to touch) the anatomical body part when the anatomical body part is supported on the support device. Preferably, the support device also comprises the aforementioned medical accessory which is at least one of the aforementioned entities.

The marking preferably fulfil at least one of the following requirements:
a) it has a predetermined spatial relationship to the anatomical body part and/or a landmark and in particular serves as a positioning aid for positioning the medical support device relative to the anatomical body part;
b) it is a marker device for detection by a navigation system as described above.

According to a preferred embodiment, all parts of the medical support device, in particular the support device and the medical accessory, are integrally formed.

DEFINITIONS

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. Instead of or additionally to operating on the principle of detecting electromagnetic reflections, the navigation system may also be configured to determine positions by evaluating medical image information. The navigation data can be stored in the permanent data memory and for example compared with data stored in said memory beforehand.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. Analytical devices in particular are used to generate the image data in apparatus-based imaging methods. The imaging methods are in particular used for medical diagnostics, to analyse the anatomical body in order to generate images which are described by the image data. The imaging methods are also in particular used to detect pathological changes in the human body. However, some of the changes in the anatomical structure, in particular the pathological changes in the structures (tissue), may not be detectable and in particular may not be visible in the images generated by the imaging methods. A tumour represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernible in the image generated by the imaging method. In addition to these tumours, referred to as "enhancing" tumours, it is thought that approximately 10% of brain tumours are not discernible on a scan and are in particular not visible to a user looking at the images generated by the imaging method.

DESCRIPTION OF THE FIGURES

In the following, an example embodiment of the inventive method will be described with reference to the figure, wherein the invention shall not be limited to the features described in connection with the figures, and wherein.

Figure 1:
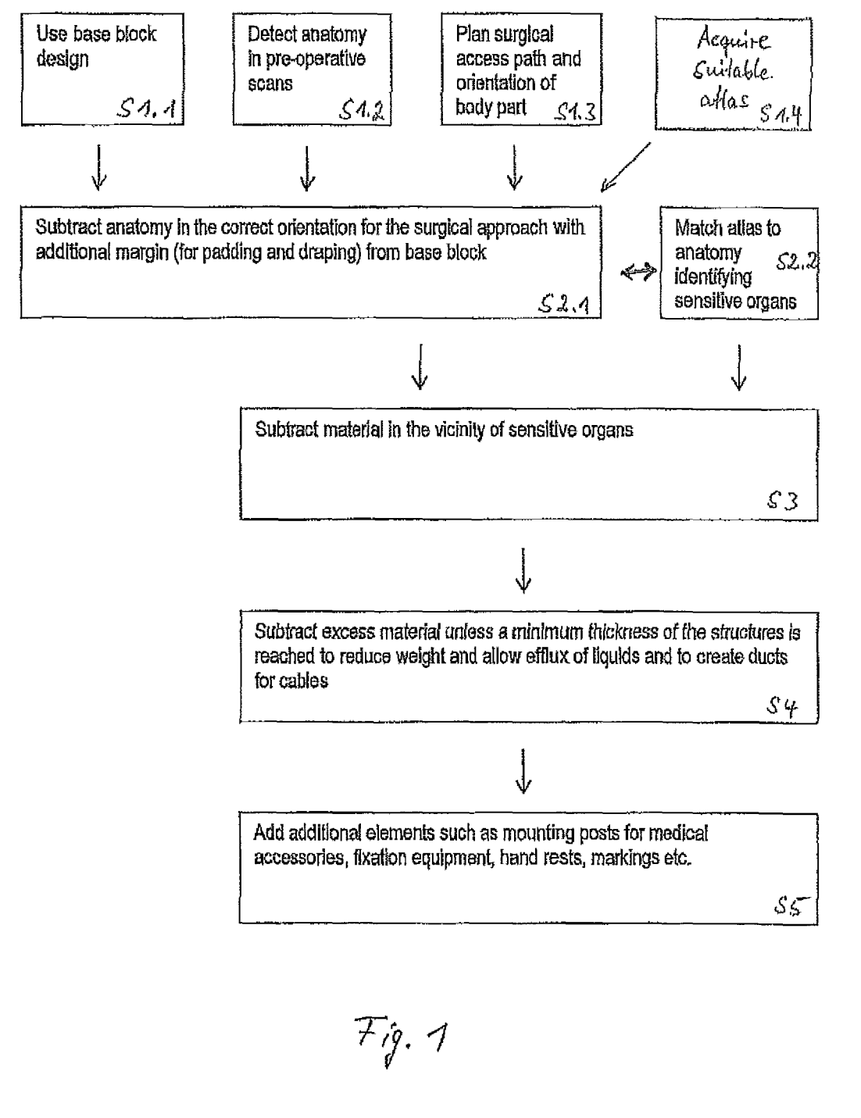
FIG. 1 is a flow diagram of an embodiment of the inventive method in which both atlas data and medical image data serve as a basis for determining the geometry of the support device.

As shown in FIG. 1, step S1.1 encompasses acquiring the initial geometry data describing an initial geometry embodied by a base block design of the material from which the support device is to be produced. Step S1.2 encompasses detecting the anatomy of the anatomical body part in pre-operative CT or MRI scans and thus relates to acquiring the aforementioned anatomical body part geometry data embodied by medical image data. Step S1.3 encompasses acquiring the aforementioned medical procedure data in order to plan a surgical access path and the orientation of the anatomical body part. Step S1.4 encompasses acquiring a suitable atlas and therefore encompasses the step of acquiring the atlas data based on in particular the medical image data acquired in step S1.2.

Step S2.1 encompasses determining the support device geometry data by subtracting, from the base block of material, the patient's anatomy determined from the atlas and advantageously also the pre-operative scans. The anatomy is subtracted from the base block preferably in the correct orientation for the envisaged medical procedure, in particular for a surgical approach, with an additional margin (which considers padding and draping of the situs). In step S2.2, the atlas data is used as an additional basis for identifying the positions of sensitive organs from the atlas matching the anatomical body part. On this basis, step S3 continues with subtracting material from the base block design (i.e. the initial geometry) in the vicinity of sensitive organs so as to leave the sensitive organs (for example the ears, the eyes, the nose or the mouth of the patient) uncovered by the support device.

Purely optional step S4 contains a step of subtracting access material from the base block design until a minimum thickness of the support structure is reached to reduce the weight of the support structure and allow a flux of liquids and great ducts for e.g. cables or other medical equipment (in particular medical instruments). Thus step S4 includes the step of acquiring accessory data.

Step S5 then continues with determining the support device geometry data based on the accessory data by for example adding additional elements to the support device such as mounting posts for medical accessories, fixation equipment, hand rests and/or markings as medical accessory.

Figure 2:
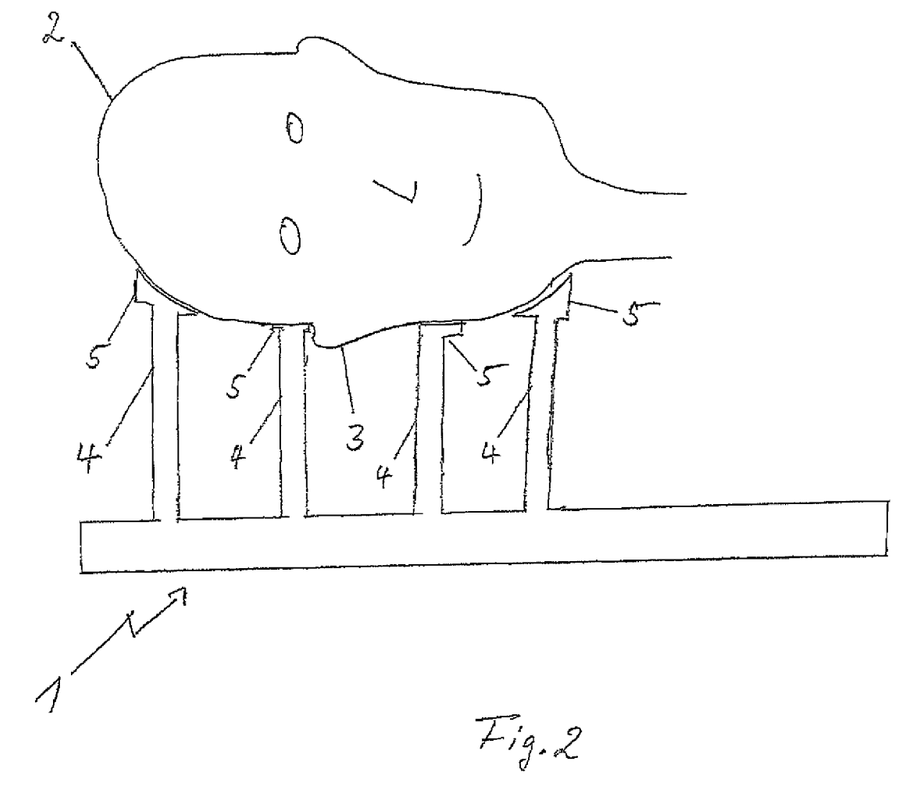
FIG. 2 is an illustration of an exemplary support device embodied by a head rest.

FIG. 2 illustrates an embodiment of the support device being a head rest 1 for a patient's head 2 which is an embodiment of the aforementioned anatomical body part. The head rest 1 comprises supports 4 which are positioned at disjunct support positions and comprise support surfaces 5 which are adapted to the geometry of the exterior surface of the patient's head 2. The support positions have been determined such that the patient's right ear 3 embodying a sensitive organ is not covered by a part of the head rest 1 so as to avoid discomfort for the patient. The head rest 1 has been produced as one integral part by one of the aforementioned generative manufacturing processes.

The invention claimed is:
1. A computer-implemented method of determining a three-dimensional shape of a medical support device for supporting an anatomical body part, the method comprising executing, by at least one processor of at least one computer, steps of:
    acquiring, at the at least one processor, body part geometry data describing a geometry of the anatomical body part;
    acquiring, at the at least one processor, medical procedure data describing a medical procedure to be carried out on the patient;
    acquiring, at the at least one processor, atlas data describing a general three-dimensional shape of the anatomical body part; and
    determining, by the at least one processor and based on the body part geometry data and the medical procedure data and from the atlas data, support device geometry data describing the geometry of the medical support device;
    wherein there is a form fit between the geometry of the medical support device and the anatomical body part with the medical support device distributing a weight of the anatomical body part of a patient.

2. The method according to claim 1, wherein the body part geometry data is acquired from or comprises medical image data describing the anatomical body part; and
    wherein determining the support device geometry data comprises:
        comparing, by the at least one processor, the medical image data to the atlas data to determine the position of an anatomical structure in a description by a body atlas described by the atlas data;
        determining, by the at least one processor, the support device geometry data based on the position of the anatomical structure in the body atlas.

3. The method according to claim 1, wherein the medical procedure data describes the position of an anatomical target region or an access path associated with the medical procedure.

4. The method according to claim 1, further comprising:
    determining, by the at least one processor and based on the atlas data, support positions of the anatomical body part.

5. The method according to claim 4, wherein
    the atlas data comprises tissue information describing properties of the tissue of the anatomical body part, and the support positions are determined, by the at least one processor, based on the tissue information.

6. The method according to claim 1, comprising:
    acquiring, at the at least one processor, initial geometry data describing an initial geometry of material for producing the medical support device;
    wherein the support device geometry data is determined, by the at least one processor, based on the initial geometry data.

7. The method according to claim 6, wherein the support device geometry data is determined, by the at least one processor, by subtracting a dataset describing a shaped volume of material from the initial geometry data.

8. The method according to claim 1, comprising:
    acquiring, at the at least one processor, accessory data comprising information about the geometry of a medical accessory; wherein
    the support device geometry data is determined, by the at least one processor, based on the accessory data.

9. The method according to claim 8,
    wherein the medical accessory is at least one of a drain part for draining a liquid, an instrument support for supporting a medical instrument, a hand rest for a user's hand, the user not being identical to the patient, a fixation unit for fixing the medical support device to a patient bed, a mounting interface for mounting the medical support device to the patient, and a marking having a predetermined spatial relationship to the anatomical body part and/or being a marker device for detection by navigation system; and
    wherein the support device geometry data contains information which describes that the medical accessory is formed integrally with the support device.

10. The method according to claim 1, wherein the support device geometry data is determined, by the at least one processor, in a digital format that makes the support device geometry data suitable as input data for a generative manufacturing process.

11. The method of claim 1 further including storing the support device geometry data on a computer readable medium for transfer to a generative forming device.

12. The method of claim 1 further comprising producing the medical support device based on the support device geometry data.

\* \* \* \* \*